United States Patent [19]
Bennett

[11] 4,079,198
[45] Mar. 14, 1978

[54] ELECTRO-ACOUSTIC IMPEDANCE BRIDGES

[76] Inventor: Michael John Bennett, 4 Clay Hill Road, Burghfield Common, Reading, RG7 3HE, England

[21] Appl. No.: 707,168

[22] Filed: Jul. 21, 1976

[30] Foreign Application Priority Data

Jul. 24, 1975 United Kingdom ............... 30942/75

[51] Int. Cl.² .......................................... A61B 10/00
[52] U.S. Cl. ................................. 179/1 N; 128/2 Z; 73/585; 73/648
[58] Field of Search ............... 179/1 N, 1 MN, 107 E; 128/2 Z; 73/553

[56] References Cited

U.S. PATENT DOCUMENTS

| | | |
|---|---|---|
| 3,294,193 | 12/1966 | Zwislocki ............................ 179/1 N |
| 3,295,513 | 1/1967 | Dippolito ............................ 179/1 N |
| 3,757,769 | 9/1973 | Arguimbau et al. ................ 179/1 N |
| 3,949,735 | 4/1976 | Klar ..................................... 179/1 N |

OTHER PUBLICATIONS

Domnitz, H., "Headphone Monitor System for Binaural Experiments," J. Ac. Soc. of Am., Aug. 1975.

*Primary Examiner*—Kathleen H. Claffy
*Assistant Examiner*—E. S. Kemeny
*Attorney, Agent, or Firm*—Beveridge, De Grandi, Kline & Lunsford

[57] ABSTRACT

An electro-acoustic impedance bridge for measuring the acoustic impedance of the human ear over a predetermined frequency range compares the magnitude and phase of the variable-frequency sound driving both the human ear and the artificial ear (acoustic coupler).

22 Claims, 6 Drawing Figures

ELECTRO-ACOUSTIC IMPEDANCE BRIDGES

The present invention is concerned with electro-acoustic impedance bridges for testing the human ear.

It is well-known that the ear presents an input impedance to an approaching sound wave. This impedance is measured in acoustic ohms, which are directly analogous to electrical ohms, and comprises three parts, namely a resistive component together with two reactive components. The ear mechanism, in common with any other mechanical system, has finite mass, stiffness and frictionally resistive components which together make up the opposition to movement.

It may be shown firstly that the mass constituents of the system, such as the masses of the ear drum, the ossicles and the fluid in the cochlea, provide the "mass reactance" which leads the velocity of the system motion by 90°, secondly that the stiffness of the eardrum and ligaments together with the stiffness of the air contained within the system act to give the lagging reactance component known as "compliance", and thirdly that the resistive component, in phase with the applied signal, results from the inherent damping in each of the components.

From the aforegoing components, it is therefore possible to obtain by vector addition an amplitude and phase angle that represent the overall system impedance for any given applied frequency. This will, of course, vary from person to person but more particularly will vary with pathological conditions. For example, one condition often incurred in old age is that in which the ossicles no longer move freely, an increased impedance then being presented. Conversely, if the ossicles have become disconnected from the eardrum then the system can be set into motion very easily and a very low impedance is presented.

One set of useful known diagnostic tests utilising the basic impedance measurement is referred to as "tympanometry". This measures the change in impedance resulting from the application of positive or negative air pressure in the outer ear. In a normal healthy person, the middle ear cleft behind the ear drum is maintained at atmospheric pressure by means of pressure equalisation through the Eustacian tube. Thus, when the air pressure in the outer ear is atmospheric, the drum can vibrate freely and a low impedance is measured. Altering the applied pressure above or below atmospheric causes the drum to stiffen and hence increase the impedance. In a pathological ear where, for example, the Eustachian tube is not working correctly, the minimum impedance will not occur when the applied pressure is atmospheric but will occur at some other pressure value. Alternatively, if for example an infection is present, the middle ear cleft can become filled with fluid and in this case no distinct impedance minimum can be measured at all.

Also useful for diagnosis is the "acoustic reflex". In the middle ear there are two small muscles attached to the ossicles. One of these, the stapedius, contracts reflexively if the ear is stimulated by a loud sound. In a normal healthy person, stimulation of either ear causes contraction of the muscles in both ears. This contraction increases the impedance of the system and can therefore be detected by monitoring the latter impedance.

The conventional manner of performing tympanomethy is to introduce a sound signal into the ear via a first tube, the sound level set up in the external auditory canal (the meatus) being detected by a microphone through a second tube and the resultant electrical signal being compared with an electrical reference signal in a bridge circuit. The level of the input sound signal is adjusted so that the microphone signal is the same as that of the reference, the bridge then being in a balanced state. A third tube is used to vary the air pressure as required for the tympanometry, the output signal of the bridge being proportional to the resulting change in impedance of the ear. All three tubes communicate with the ear via a common air-tight probe.

In this known apparatus, the sound signal is generated by an oscillator operating at one or sometimes two specific frequencies (usually 220 Hz). The use of a fixed frequency bridge has the disadvantage, however, that the frequency response of the tubing, microphones etc. limits their use to the specific frequency or frequencies for which the apparatus is calibrated.

It has been appreciated, however, that it would be of considerable advantage from a diagnostic point of view to be able to monitor the impedance over a complete sweep of at least a portion of the audible frequency range. Inter alia, this would enable resonance effects, which are of course highly frequency specific, to be monitored. Furthermore, by determination of the frequency characteristic of the impedance, one is able to accurately identify the nature, position and extent of many pathological conditions not capable of being accurately diagnosed by the above described fixed frequency test.

In accordance with the present invention, there is provided an electro-acoustic impedance bridge apparatus comprising an acoustic coupler whose acoustic impedance is representative of the acoustic impedance of the normal human ear over a predetermined frequency range, a pair of probes, one for connection to the external auditory canal of an ear to be tested and the other attached to the acoustic coupler, a variable frequency sound generator for applying to both probes sound signals of equal frequency within said predetermined frequency range, and means coupled to said probes for comparing the resulting sound levels prevailing in the external auditory canal of the test ear and in the acoustic coupler.

Preferably, the variable frequency sound generator includes means for sweeping the frequency of said two sound signals through said predetermined frequency range.

Advantageously, the apparatus includes means which enable the frequency sweep to be stopped at any desired frequency within said predetermined frequency range.

To enable the apparatus to take account of the variation in the acoustic impedance of the human ear with frequency, the variable frequency sound generator preferably includes means for automatically adjusting the level of said two sound signals in dependence upon the frequency of these two signals, such that the sound levels of the sound signals applied to the two probes changes with the frequency of these sound signals in accordance with a predetermined characteristic.

Alternatively, the variable frequency sound generator may include a feedback control circuit for automatically adjusting the level of the two input sound signals such as to maintain the sound level in the acoustic coupler, and hence in the test ear, at a substantially constant level throughout said predetermined frequency range.

The invention is described further hereinafter, by way of example, with reference to the accompanying drawings, in which:

FIG. 4a is a circuit diagram for illustrating the principle of a variable gain amplifier of FIG. 4.

Figure 1:
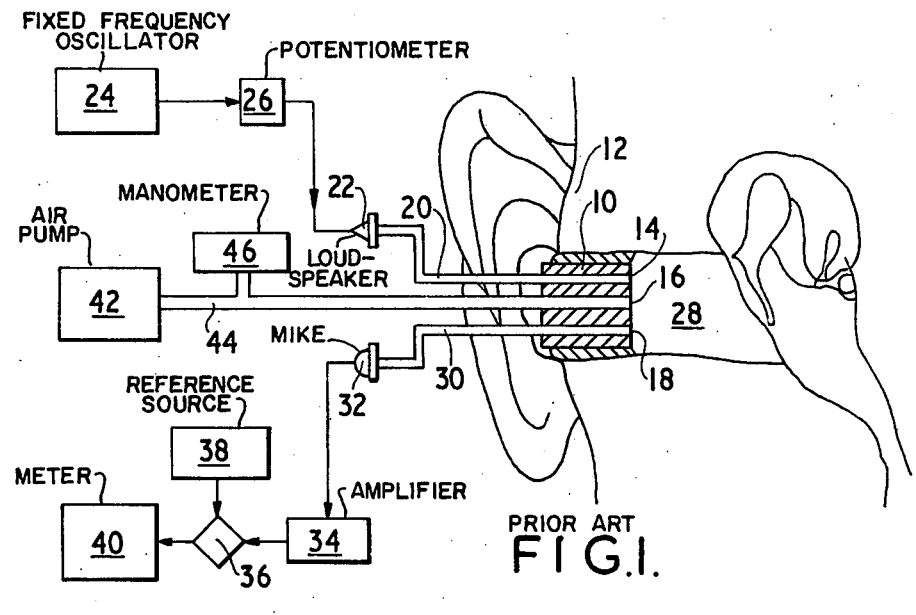
FIG. 1 is a diagrammatic illustration of the principal components of a known electro-acoustic impedance bridge.

With reference to FIG. 1, the known electro-acoustic bridge comprises a probe 10 which is adapted to be fitted in a human ear 12 in an air-tight manner and which contains three open-ended passages or tubes 14, 16, 18. The passage 14 is coupled by way of a waveguide 20 to a loudspeaker 22 driven by a fixed frequency oscillator 24 via a potentiometer 26 whereby a probe tone can be introduced to the ear. The fixed frequency is conventionally 220 Hz although 660 Hz and 825 Hz have also been used. The sound level set up in the external auditory canal 28 (the meatus) is transmitted by the passage 18 and a second waveguide 30 to a microphone 32 where an electrical signal corresponding to said sound level is generated. The latter signal is transferred via an amplifier 34 to a conventional bridge circuit 36 where it is compared with the signal from a reference voltage source 38, the reading on a meter 40 indicating the balance condition of the bridge 36. The bridge is initially brought into a balanced condition by adjusting the level of the probe signal by means of the potentiometer 26 to make the microphone signal equal to the reference signal.

For performing tympanometry tests, the third passage 16 in the ear probe 10 is connected to an air pump 42 by a pipe 44, a manometer 46 being provided for indicating the level of the pressure applied. The applied pressure can thus be varied, the resulting change in the impedance of the ear being indicated by the balance meter 40 of the bridge. It will be noted that the aforegoing type of bridge measures only the impedance vector amplitude and not its phase angle.

Figure 2:
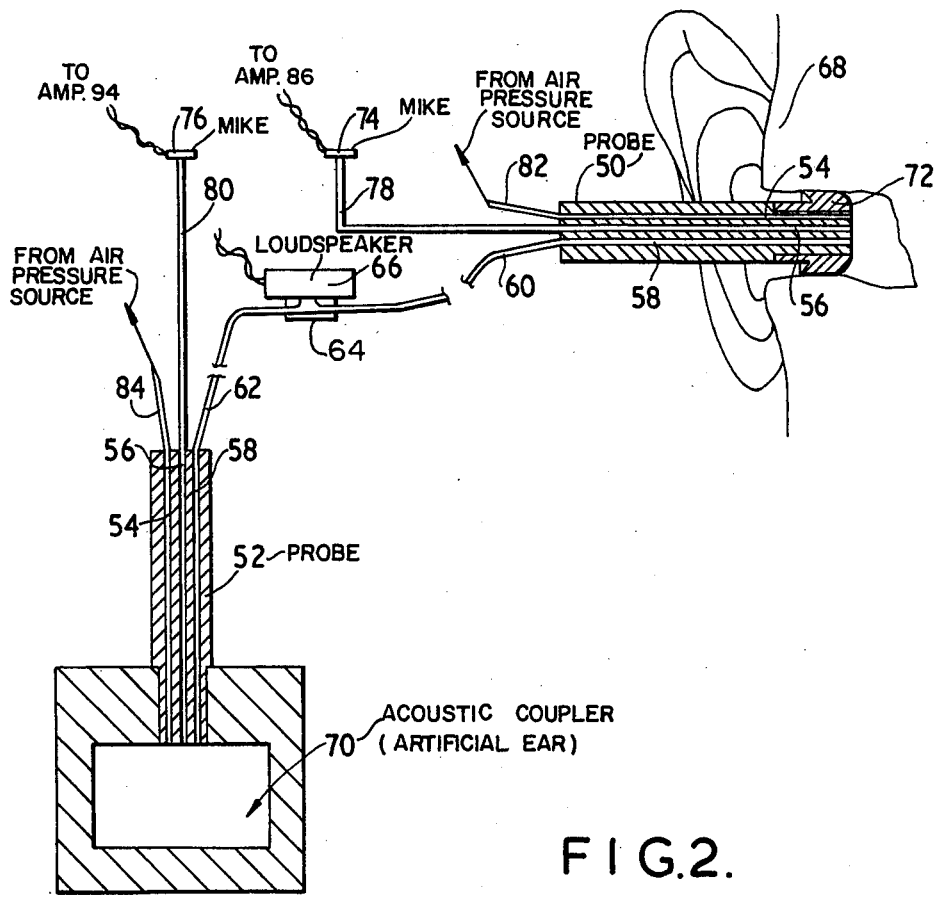
FIG. 2 is a diagrammatic illustration of the acoustic portion of an electro-acoustic impedance bridge apparatus in accordance with the present invention.

FIG. 2 illustrates the acoustic part of an apparatus in accordance with the invention which includes a pair of identical probes 50 and 52, each of which contains three passages or tubes 54, 56, 58 having equal internal diameters of the order of 2mm. The tubes 58 of the probes 50,52 are respectively connected by tubes 60,62, of equal internal diameter to the tubes 58, to a T-piece 64 which is acoustically coupled to a miniature high impedance loudspeaker 66 to enable an equal sound level to be introduced to both an ear 68 under test via the test probe 50 and to an acoustic coupler 70 via the reference probe 52. The test probe 50 is sealed to the test ear in an air-tight manner by the use of a plastics tip 72 and the reference probe 52 is sealed into the acoustic coupler 70.

In its simplest form, the acoustic coupler 70 can comprise a 1.7 cc cavity formed in a block of a suitable material. However, the acoustic impedance of the acoustic coupler 70 should as far as possible be representative of the impedance of a human ear over the range of test frequencies concerned. This can be achieved by the provision of additional bores (not shown) communicating with the cavity. Acoustic couplers or so-called "artifical ears" of this nature have already been developed for the calibration of telephone receivers and the like.

The second passage or tube 56 of each probe 50,52 is connected to a respective electret microphone 74,76, again by way of tubing 78,80 of equal internal diameter.

The third passage or tube 54 of each probe 50,52 is connected by means of identical tubing 82,84 to a common pressurisation source (not shown). Preferably, each tube 54 contains an acoustic resistor (not shown) for preventing the volume of the pressurisation system affecting the sound monitoring system.

Figure 3:
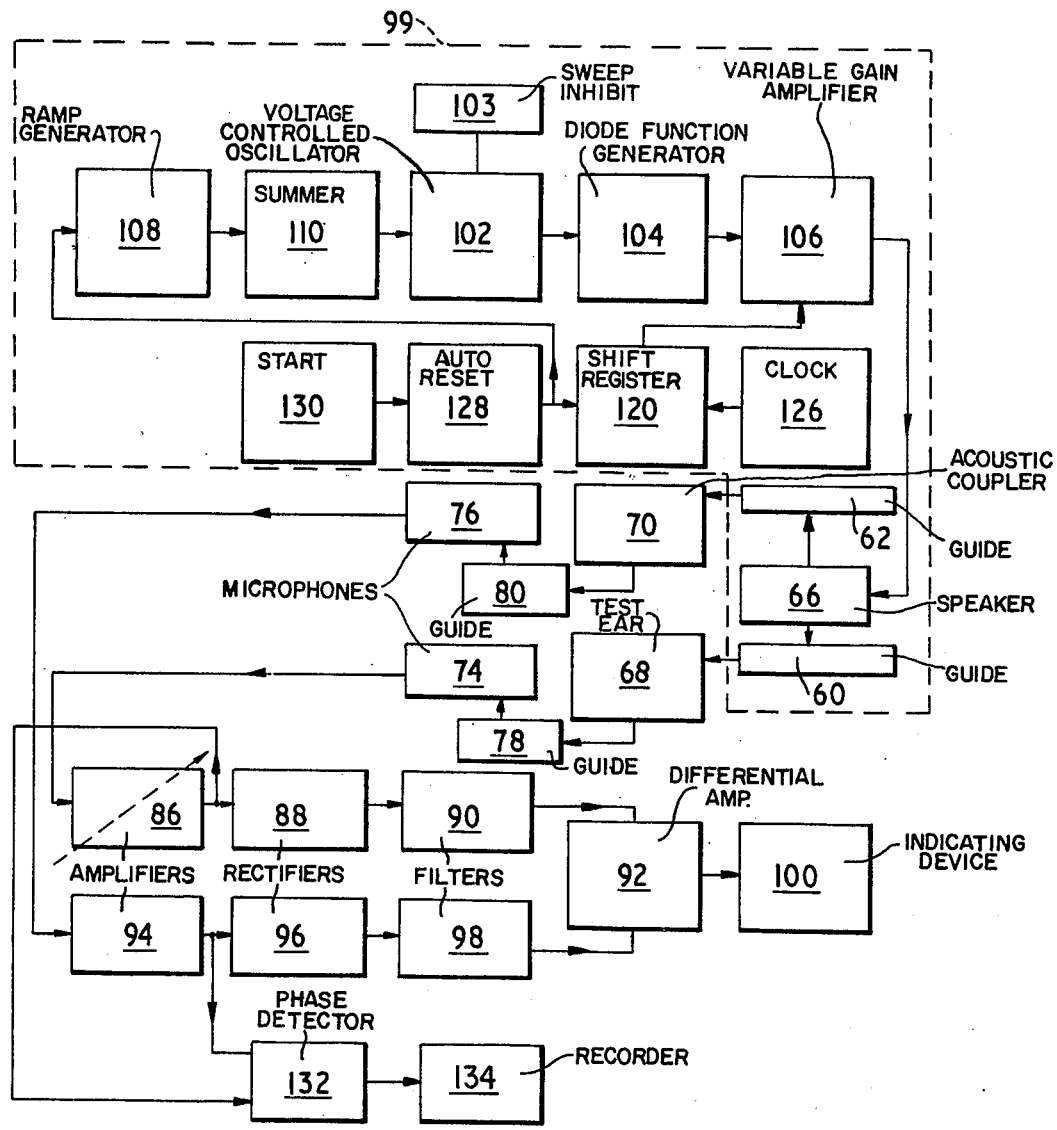
FIG. 3 is a block diagram of one complete embodiment of an electro-acoustic impedance bridge apparatus in accordance with the present invention.

As shown in FIG. 3, the signals from the two microphones 74,76 are connected to two identical signal conditioning channels of a receiving section. The microphone 74 is connected via a low-noise amplifier 86, a rectifier 88 and a smoothing filter 90 to one input of a differential amplifier 92. Similarly, the microphone 76 is connected to the other input of the differential amplifier 92 via an identical low-noise amplifier 94, rectifier 96 and smoothing filter 98. The two DC signals produced by these two conditioning channels are combined in the difference amplifier 92, the difference being displayed on an indicating and recording device 100.

In an alternative embodiment, the difference amplifier 92 is replaced by a dividing circuit whereby to obviate the disadvantage incurred with the use of a difference amplifier that the output sensitivity of the apparatus varies in dependence upon the level of the input sound signal.

The aforegoing receiving part of the apparatus is thus designed to respond to and indicate any difference between the impedances of the test ear and the reference cavity or coupler. As stated above, it is a requirement of the present apparatus that this impedance comparison can be monitored over a predetermined range of frequencies. It has been appreciated, however, that the achievement of this object is complicated by several factors. Firstly, it is known that the impedance of the ear changes with frequency so that, at least over part of the acoustic range of the ear, the signal picked up by the microphone 74 can be expected to vary with alteration in frequency. This can give rise to signal to noise problems as well as problems overloading of components such as the microphone 74. Secondly, although it is desirable to set up a sound level in the meatus which is as loud as possible for signal to noise purposes, the sound level must not be too loud or the acoustic reflex will be stimulated. Again, the situation is complicated by the fact that the acoustic reflex is frequency sensitive and is therefore stimulated at different sound levels for different frequencies. Thirdly, the ear exhibits resonance characteristics at certain frequencies giving rise to output peaks at those frequencies.

These problems are overcome in the present apparatus by the provision of means for automatically changing the input sound level applied to the test ear and reference cavity in steps as the frequency range is swept through. The manner in which the individual sound levels corresponding to different frequencies are chosen is discussed further below.

As illustrated in the block diagram of FIG. 3, a variable frequency input signal is applied to both the test ear 68 and the acoustic coupler 70 by means of a variable frequency sound generator 99 which in the present embodiment includes by a voltage controlled oscillator 102. As described further below with reference to FIG. 4, the output of the oscillator is shaped by a diode function generator 104 and applied to a digitally controlled gain amplifier 106 which supplies to the loudspeaker 66 an input whose level is changed with the frequency. The output frequency of the voltage controlled oscillator 102 is arranged to be linearly dependent upon a DC input control voltage produced by a ramp generator 108. Since the input test signal is required to commence at a frequency above zero, in this case 60 Hz, a constant voltage of a level to produce a 60 Hz frequency from the voltage controlled oscillator 102 is added to the ramp voltage by a summer 110.

Figure 4:
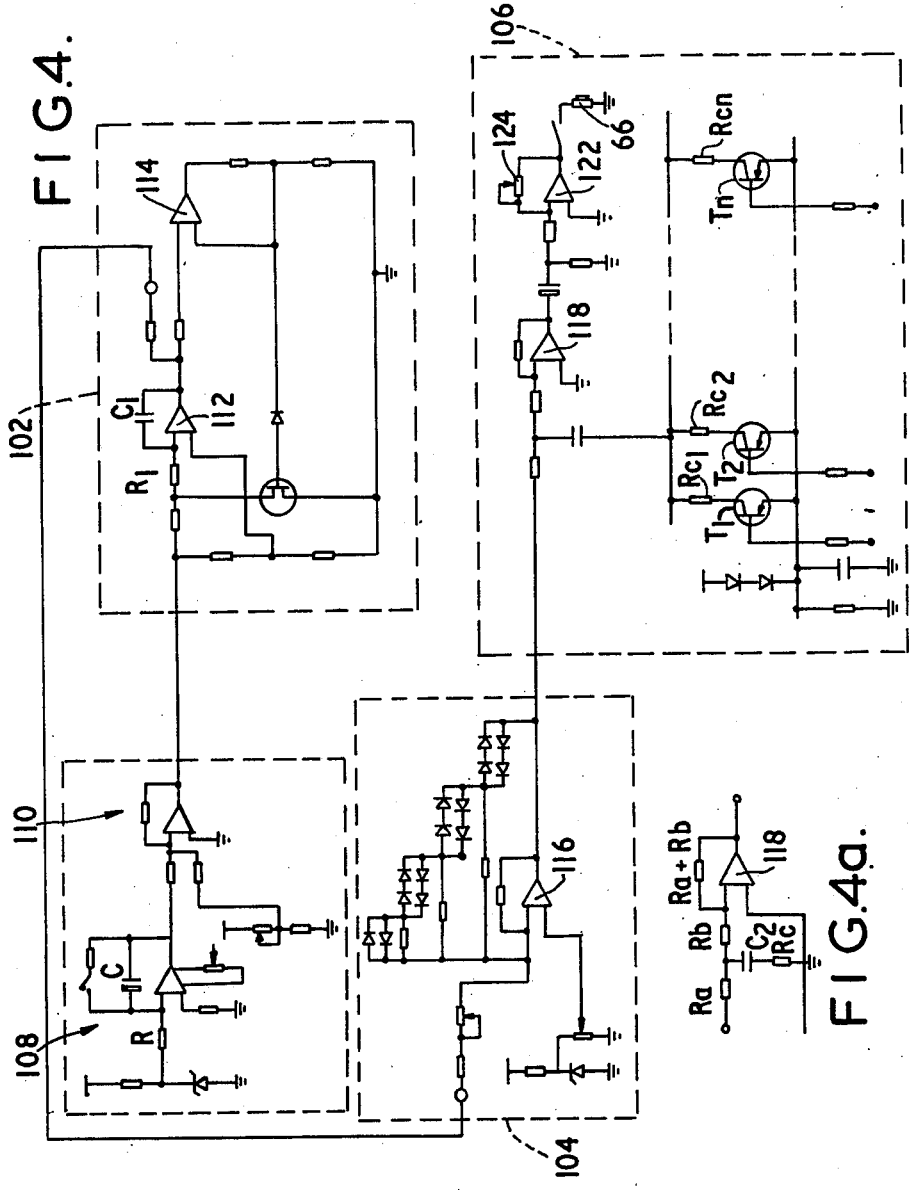
FIG. 4 is a circuit diagram showing details of several of the blocks of FIG. 3.

FIG. 4 illustrates in more detail preferred embodiments of the ramp generator 108 and summer 110, the voltage controlled oscillator 102, the diode function generator 104 and the variable gain amplifier 106.

The ramp generator 108 is in the form of an integrator whose output voltage is proportional to the integral with respect to time of the input voltage whereby for a constant input voltage a linear output ramp results, whose ramp rate is set by the CR time constant and which can be reset to zero output by short-circuiting the feedback capacitor C. The integrator output is then summed in the summer 110 with a constant voltage proportional to 60 Hz to produce the required control ramp voltage output.

The voltage controlled oscillator 102 produces a triangular waveform output whose frequency is linearly dependent upon the positive DC input control voltage. This is achieved by the use of a differential amplifier 112 connected as an integrator which ramps at a rate determined by the input control voltage and the time constant $C_1 R_1$. The integrator 112 feeds a high slew rate comparator 114. At the instant the output of the comparator 114 switches between its saturation limits, the direction of the ramp also changes so as to produce a triangular wave output.

The diode function generator 104 serves to modify into a sine wave the constant amplitude triangular waveform from the voltage controlled oscillator 102. This is achieved by the use of an operational amplifier 116 whose resistive feedback, and hence whose gain, is controlled by amplifying some parts of the triangular waveform more than others. As the output voltage of the circuit increases, it overcomes the bias potential of a plurality of parallel diode sets in the feedback path and so effectively switches in parallel resistance which decreases the gain of the amplifier 116. Hence the apex of each triangular waveform is flattened and the sides boosted so as to produce a substantially sinusoidal output waveform.

The variable gain amplifier 106 comprises an inverting amplifier 118 whose forward path resistive element $R_c$ (see FIG. 4a) can be varied to change the amplifier gain. The forward path resistance in FIG. 4a comprises the T-element formed by the resistors $R_a$, $R_b$ and $R_c$ and has a total resistance given by: $R = R_a R_b / R_c + R_a + R_b$ The break frequency due to the capacitor $C_2$ is arranged to be well below the operating frequency so that $C_2$ acts as a DC block maintaining the DC bias for the amplifier 118. It is apparent that by changing the value of the single element $R_c$ the total value of R, and hence the amplifier gain, can be changed. As shown in FIG. 4, a plurality of resistors $R_{c1}$, $R_{c2}$ ... $R_{cn}$ of predetermined value are provided, each of which is in series with an associated trasistor switch $T_1$, $T_2$ ... $T_n$. The switches $T_1$ ... $T_n$ are individually, sequentially controllable by a shift register 120 for selecting corresponding discrete amplification levels throughout the frequency sweep.

The final overall amplitude emanating from the amplifier 118 is boosted to the required drive level for the loudspeaker 66 by a further amplifier 112 whose gain can be preset by a variable resistor 124.

The shift register 120, for example having 15 bits, is driven by a 1 Hertz clock 126, its operation being synchronised with the operation of the ramp generator 108 by means of pulses from a start and automatic reset circuit 128 which are initiated by means of a start button 130 at the commencement of the test. Thus, as the voltage controlled oscillator 102 sweeps through the frequency range, the shift register 120 is also actuated. The resulting bit shifting down the register is used to select resistors $R_{c1}$ ... $R_{cn}$ in turn and so produce the required output to the loudspeaker 66.

The resistors are chosen to result in an input sound level characteristic at the loudspeaker 66 which compensates for the frequency dependent impedance characteristic of the human ear whilst maintaining, throughout the frequency range under test, the input sound level below that at which the acoustic reflex would be stimulated. Ideally, the input sound level characteristic is selected such that, for a normal healthy ear, the sound pressure level set up in the external auditory canal 28 is at a substantially constant level. The impedance of the human ear changes with frequency such that the input signal level, in for example the test probe 50, would have to be increased by approximately 6 dB per octave in order to obtain a constant level output in the external auditory canal 28. Acoustic couplers which are designed to represent the human ear have an impedance characteristic which is substantially identical to that of the ear. Thus, one way in which the resistors $R_{c1}$ ... $R_{cn}$ can be chosen is to connect the acoustic coupler to the loudspeaker 66 by way of an input waveguide and to connect an output waveguide to a microphone and electrical measuring device, the values of the resistors $R_{c1}$ ... $R_{cn}$ being selected experimentally to give a substantially constant signal in the acoustic coupler throughout the range of required input test frequencies. This has the effect of increasing the input signal level by 6 dB per octave over the test frequency range, for example 60 Hz to 7.5 kHz. The relative level characteristic of the input signal having been set up in this manner, the overall level is then set by the variable gain amplifier 122 so that the acoustic reflex is not stimulated at any frequency in the test range. It is known that the curve of sound level at which the reflex is stimulated vs. frequency exhibits a minimum at about 1 kHz. If the input sound level at 1 kHz is set by the resistor 124 to be just below that at which the acoustic reflex in a typical human ear is stimulated, the shape of the latter curve is such that the acoustic reflex will not be stimulated by the sound level at any other test frequency.

Clearly, the more closely the impedance of the ear is represented over the test frequency by the acoustic coupler the better since then the deviation between the microphone signals, and hence the final output, will then be kept as flat as possible.

In operation, the differential amplifier 92 compares the rectified signals from the two microphones 74, 76 over the whole test frequency range, the result of the comparison being continuously recorded on the recorder 100. A second recorder 134 connected to a phase detector 132 enables the phase difference between the signals from the two low noise amplifiers 86,94, and hence from the two microphones 74,76, to be monitored. From the recorded outputs, pathological conditions of the ear can be diagnosed and identified.

The present apparatus can be adapted for performing the known tympanometry tests by arranging for the sweep to be stopped by a sweep inhibit device 103 for the duration of the test at any desired frequency within the aforementioned frequency range, the air pressure being altered via the tubes 82,84. By this test, a plot is obtainable both of the variation of impedance amplitude and of phase in response to this pressure change.

Similarly, by stopping the sweep at a desired frequency, one can determine the change in amplitude and phase that occurs for that frequency when the other ear is subjected to a loud sound to stimulate its acoustic reflex. This is known as contra-lateral reflex testing. Also, by increasing the probe tone volume, it is possible to stimulate the ear under test to produce the reflex and simultaneously to monitor it. This is known as ipsi-lateral reflex testing. The known bridges have the disadvantage that they can only make the latter measurement at certain fixed frequencies (e.g. 2 kHz, 1 KHz and 500 Hz) because of interaction between the ipsi-lateral stimulating tone, which is produced from an additional loudspeaker source, and the probe tone.

In another modification, means are provided to enable the gain of the test ear receiving channel to be varied at a point immediately after the low-noise amplifier 86. This permits the overall output from the ear under test to be pre-adjusted to initially allow for the variation in size of the subject's external ear canal, a feature which largely accounts for the level of the sound pressure set up in the canal.

Figure 5:
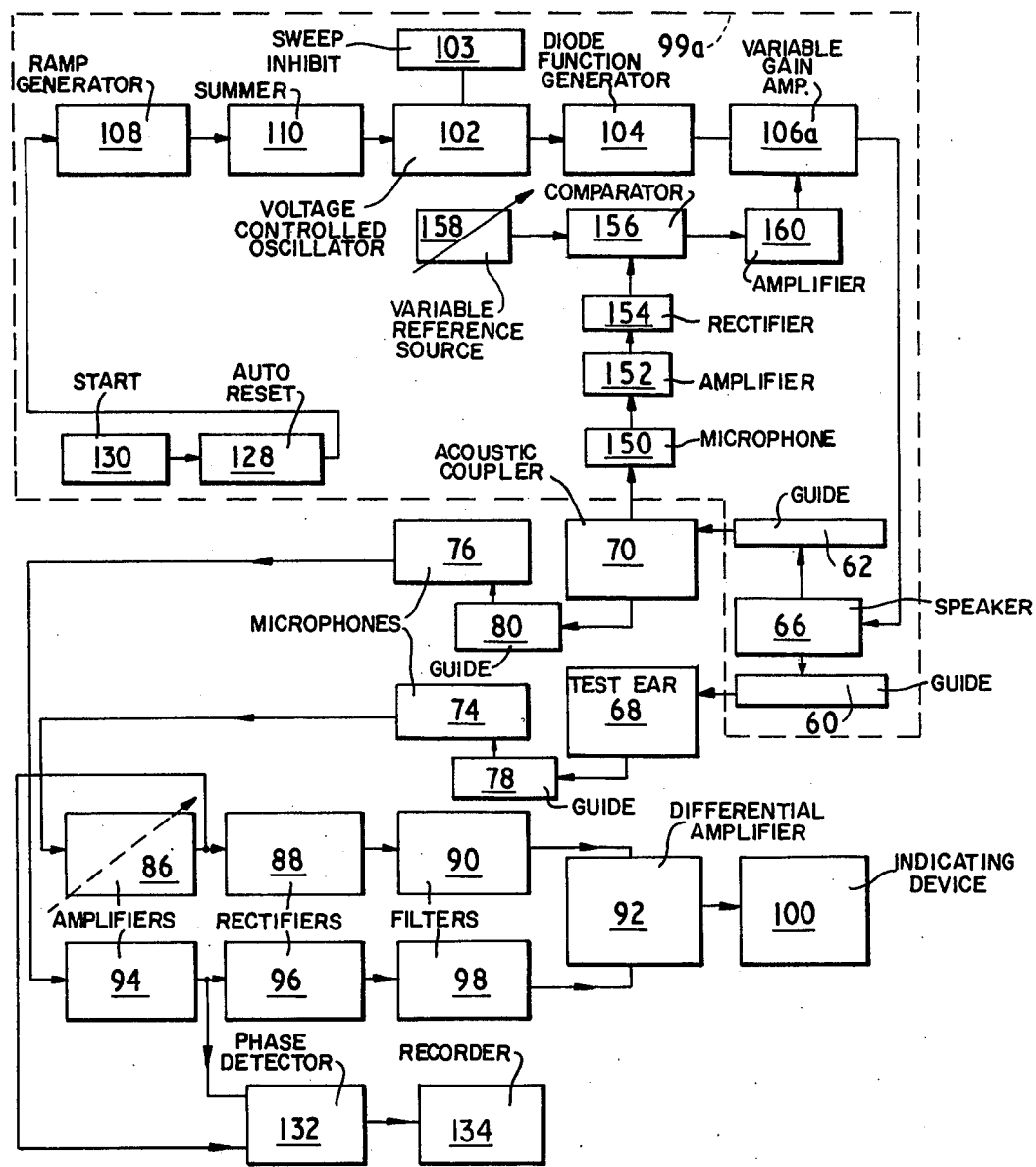
FIG. 5 is a block diagram of a second complete embodiment in accordance with the present invention.

FIG. 5 illustrates an alternative embodiment of bridge apparatus embodying the invention. In FIG. 5, all those integers which are common to the embodiment of FIG. 3 have been given the same reference numerals. The essential difference between the embodiments of FIGS. 3 and 5 lies in the manner in which the gain of the variable gain amplifier driving the loudspeaker 66 is controlled. In the FIG. 5 embodiment, a feedback circuit is used to maintain the signal level in the acoustic coupler 70 at a substantially constant level. For this purpose a further microphone 150 is mounted in the base of the cavity of the coupler 70, the output of the microphone 150 being amplified in an amplifier 152 before being rectified at 154 and applied to one input of a comparator 156. The other input of the comparator receives a signal from a pre-set variable reference source 158. The resulting error signal from the comparator is passed, via an amplifier 160, to an input of a variable gain amplifier 106a whose gain is determined by the instantaneous magnitude of the latter input and hence by the magnitude of the error signal.

In the FIG. 5 arrangement, therefore the gain of the amplifier 106a is continuously varied by the feedback circuit to maintain the sound level in the acoustic coupler 70 at a substantially constant level throughout the frequency range swept by the oscillator 102.

I claim:

1. An electro-acoustic impedance bridge apparatus comprising an acoustic coupler whose acoustic impedance is representative of the acoustic impedance of the normal human ear over a predetermined frequency range, a pair of probes, one for connection to the external auditory canal of an ear to be tested and the other attached to the acoustic coupler, a variable frequency sound generator for applying to both probes sound signals of equal frequency within said predetermined frequency range, means in said variable frequency sound generator for sweeping the frequency of said two sound signals through said predetermined frequency range, means for varying the input sound levels applied to the test ear and the acoustic coupler by said variable frequency sound generator as the frequency range is swept through, and comparator means coupled to said probes for comparing the resulting sound levels prevailing in the external auditory canal of the test ear and in the acoustic coupler.

2. An apparatus according to claim 1, having means enabling the frequency sweep to be stopped at any desired frequency within said predetermined frequency range.

3. An apparatus according to claim 1, in which said means for varying the input sound levels applied by the variable frequency sound generator includes means adapted to automatically adjust the level of said two sound signals in dependence upon the frequency of these two signals, such that the sound levels of the sound signals applied to the two probes changes with the frequency of these sound signals in accordance with a predetermined characteristic.

4. An apparatus according to claim 3, in which said predetermined characteristic is such that the sound levels of the sound signals applied to the two probes increases by 6 dB per octave, with increasing frequency.

5. An apparatus according to claim 3, in which the level adjusting means for said two sound signals comprises a variable gain amplifier.

6. An apparatus according to claim 5, in which the variable gain amplifier has a plurality of individually selectable gain steps and, the apparatus further includes a shift register which sequentially selects the gain steps of the variable gain amplifier and which is adapted to shift in accordance with the frequency of the two sound signals.

7. An apparatus according to claim 1, in which said means for varying the input sound levels applied by the variable frequency sound generator includes a feedback control circuit which automatically adjusts the level of the two input sound signals such as to maintain the sound level in the acoustic coupler at a substantially constant level throughout said predetermined frequency range.

8. An apparatus according to claim 7, in which the feedback control circuit includes a variable gain amplifier controlling the level of said two input sound signals, the gain of the latter amplifier being determined by the magnitude of an error signal obtained from the comparison of the sound level in the acoustic coupler with a preset reference level.

9. An apparatus according to claim 5, in which the overall level of the signal emanating from the variable gain amplifier is adjustable to enable the sound level applied to the test ear probe, at all frequencies in said predetermined range, to be kept below that at which the acoustic reflex would be stimulated.

10. An apparatus according to claim 5, in which the variable frequency sound generator includes a voltage controlled oscillator for driving said variable gain amplifier with a signal of variable frequency.

11. An apparatus according to claim 10, in which the variable frequency signal produced by the voltage controlled oscillator is of triangular waveform and a diode function generator is included between the voltage controlled oscillator and the variable gain amplifier for converting said triangular waveform into a corresponding sinusoidal waveform.

12. An apparatus according to claim 10, further comprising a ramp generator for driving the voltage controlled oscillator such that the latter produces an output signal of linearly increasing frequency.

13. An apparatus according to claim 12, further comprising summing means enabling a constant DC level to be added to the output of the ramp generator whereby the frequency sweep of the voltage controlled oscillator starts at a frequency greater than zero.

14. An apparatus according to claim 1, in which the variable frequency sound generator includes a loudspeaker for generating said two sound signals, and respective waveguides connecting the loudspeaker to said two probes.

15. Apparatus according to claim 14, in which the waveguides connecting the loudspeaker to the probes comprise tubes of equal internal diameter.

16. An apparatus according to claim 1, in which the sound level comparison means includes two microphones connected by respective waveguides to passages in the two probes for generating, in use of the apparatus, electrical signals corresponding to the sound levels in the external auditory canal of the test ear and the acoustic coupler, respectively.

17. An apparatus according to claim 16, in which the sound level comparison means further includes first and second signal conditioning channels respectively connected to the two microphones, each channel containing an amplifier and a rectifier for providing a DC signal proportional to the output of the associated microphone.

18. An apparatus according to claim 17, further including a difference amplifier for comparing the two DC signals obtained from the two signal conditioning channels.

19. An apparatus according to claim 17, including a signal divider for comparing the two DC signals obtained from the two signal processing channels.

20. Apparatus according to claim 17, including a phase detector for comparing the phases of the outputs of the two microphones.

21. Apparatus according to claim 17, in which the gain of at least that one of the amplifiers, which is in the signal conditioning channel associated with the test ear, is variable to enable the overall output from this channel to be adjusted.

22. An electro-acoustic impedance bridge comprising an acoustic coupler whose acoustic impedance is representative of the acoustic impedance of the normal human ear over a predetermined audio frequency range, a pair of probed, one for connection to the external auditory canal of an ear to be tested and the other attached to the acoustic coupler, a variable frequency sound generating means for applying to both probes sound signals whose frequency is swept through said predetermined frequency range, means for varying the input sound levels applied to the test ear and the acoustic coupler by said variable frequency sound generating means as the predetermined frequency range is swept through, and means coupled to said probes for comparing the resulting sound levels prevailing in the external auditory canal of the test ear and in the acoustic coupler.

* * * * *